US009683262B2

(12) United States Patent
Johnson

(10) Patent No.: US 9,683,262 B2
(45) Date of Patent: Jun. 20, 2017

(54) METHODS OF ISOLATING AND PURIFYING CD8 T CELLS

(71) Applicant: Raymond M. Johnson, Indianapolis, IN (US)

(72) Inventor: Raymond M. Johnson, Indianapolis, IN (US)

(*) Notice: Subject to any disclaimer, the term of this patent is extended or adjusted under 35 U.S.C. 154(b) by 0 days.

(21) Appl. No.: 14/642,546

(22) Filed: Mar. 9, 2015

(65) Prior Publication Data
US 2015/0252420 A1    Sep. 10, 2015

Related U.S. Application Data

(63) Continuation-in-part of application No. 14/215,144, filed on Mar. 17, 2014.

(60) Provisional application No. 61/950,386, filed on Mar. 10, 2014.

(51) Int. Cl.
C12Q 1/00         (2006.01)
C12Q 1/68         (2006.01)
C12N 5/07         (2010.01)
C12N 5/16         (2006.01)
G01N 33/569       (2006.01)
C07K 16/28        (2006.01)
C12N 5/00         (2006.01)
C12N 5/0783       (2010.01)

(52) U.S. Cl.
CPC ............ C12Q 1/6881 (2013.01); C07K 16/28 (2013.01); C12N 5/0087 (2013.01); C12N 5/0638 (2013.01); G01N 33/56972 (2013.01); C07K 2317/34 (2013.01); G01N 2333/295 (2013.01); G01N 2333/5437 (2013.01); G01N 2333/70517 (2013.01)

(58) Field of Classification Search
CPC ........ C12Q 1/6844; C12Q 1/689; C12Q 1/02; C12Q 1/025; C12Q 2600/158; C12Q 2600/112; C12Q 2600/16; C12Q 2525/161
See application file for complete search history.

(56) References Cited

PUBLICATIONS

Igietseme et al. Role of T lymphocytes in the pathogenesis of Chlamydia disease. J Infect Dis 200: 926-934 (2009). USA.
Murthy et al. Tumor necrosis factor alpha production from CD8+ T cells mediates oviduct pathological sequelae following primary genital Chlamydia muridarum infection. Infect Immun 79: 2928-2935 (2011). USA.
Johnson et al. An atypical CD8 T-cell response to Chlamydia muridarum genital tract infections includes T cells that product interleukin-13. Immunology 142: 248-257 (2014). USA.
(Continued)

Primary Examiner — Ja'Na Hines
(74) Attorney, Agent, or Firm — Reichel Stohry LLP; Natalie J. Dean; Mark C. Reichel

(57) ABSTRACT

Methods are provided for isolating CD8+ T cells. Furthermore, methods for purifying a subset of IL-13 expressing CD8 T cells are provided, such methods comprising the steps of marking the CD8+ T cells by labeling CD8, or selectively removing non-CD8 cells, and then purifying a subset of IL-13 expressing CD8+ T cells by marking a human biomarker such as C10orf128. Related antibodies and antiserums are also described, such antibodies related to a cell surface domain peptide for biomarker C10orf128, and human homologs of related mouse "activated" CD8IL-13 cell surface biomarkers Tm4sf19 and 1830127L07Rik.

6 Claims, 8 Drawing Sheets

(56) References Cited

PUBLICATIONS

Fuschiotti et al. Effector CD8+ T cells in systemic sclerosis patients produce abnormally high levels of interleukin-13 associated with increased skin fibrosis. Arthritis Rheum 60: 1119-1128 (2009). USA.

Fuschiotti et al. Interleukin-13-producing CD8+ T cells mediate dermal fibrosis in patients with systemic sclerosis. Arthritis Rheum 65: 236-246 (2013).

| Gene Symbol | p-value (CD8IL13+ vs. CD8IL13- and allo CD8) | Fold-Change (CD8IL13+ vs. CD8IL13- and allo CD8) | p-value (CD8IL13+ vs. CD8IL13-) | Fold-Change (CD8IL13+ vs. CD8IL13-) | p-value (CD8IL13+ vs. allo CD8) | Fold-Change (CD8IL13+ vs. allo CD8) | same direction | sig | >3 |
|---|---|---|---|---|---|---|---|---|---|
| 1810011H11Rik | 1.52E-15 | 22.31 | 2.12E-15 | 24.85 | 8.19E-14 | 20.03 | Y | 1 | 1 |
| Amelx | 8.75E-12 | 10.68 | 1.57E-10 | 7.75 | 4.13E-11 | 14.71 | Y | 1 | 1 |
| Dclk3 | 8.80E-12 | 6.20 | 3.77E-11 | 5.73 | 1.37E-10 | 6.72 | Y | 1 | 1 |
| Mtmr7 | 8.29E-09 | 5.40 | 5.86E-09 | 6.24 | 5.72E-07 | 4.67 | Y | 1 | 1 |
| Ccr8 | 2.15E-08 | 8.90 | 4.58E-08 | 8.89 | 4.49E-07 | 8.91 | Y | 1 | 1 |
| Arntl | 5.51E-07 | 6.84 | 3.00E-08 | 12.80 | 5.00E-04 | 3.65 | Y | 1 | 1 |
| Sulf2 | 1.84E-06 | 10.10 | 2.14E-04 | 4.84 | 1.12E-06 | 21.07 | Y | 1 | 1 |
| Prl2c5 | 9.94E-05 | 8.88 | 2.06E-04 | 8.54 | 7.44E-04 | 9.24 | Y | 1 | 1 |
| Hpgds | 1.20E-04 | 8.11 | 4.49E-04 | 6.86 | 5.25E-04 | 9.60 | Y | 1 | 1 |

FIG. 6

| Gene Symbol | gene title |
|---|---|
| 1810011H11Rik | uncharacterized protein LOC69069 precursor |
| Amelx | amelogenin X chromosome |
| Dclk3 | doublecortin-like kinase 3 |
| Mtmr7 | myotubularin related protein 7 |
| Ccr8 | chemokine (C-C motif) receptor 8 |
| Arntl | aryl hydrocarbon receptor nuclear translocator-like |
| Sulf2 | sulfatase 2 |
| Prl2c5 | prolactin family 2, subfamily c, member 5 |
| Hpgds | hematopoietic prostaglandin D synthase |

METHODS OF ISOLATING AND PURIFYING CD8 T CELLS

PRIORITY CLAIM

This application is related to and claims the priority benefit of: (a) and is a continuation-in-part application of U.S. patent application Ser. No. 14/215,144 to Johnson, filed Mar. 17, 2014, which claims the priority benefit of U.S. Provisional Application Ser. No. 61/787,048 to Johnson, filed Mar. 15, 2013; and (b) U.S. Provisional Patent Application Ser. 61/950,386 to Johnson, filed Mar. 10, 2014. The content of each of the aforementioned applications are hereby expressly incorporated herein by reference in their entireties into this disclosure.

STATEMENT REGARDING FEDERALLY SPONSORED RESEARCH

This invention was made with government support under R01 AI070514 and RO1 AI113103 awarded by the National Institutes of Health. The United States Government has certain rights in the invention.

BACKGROUND

*Chlamydia* infection is the most common sexually transmitted disease, responsible for about 2.8 million cases a year in the US. Untreated *Chlamydia* infections can ascend into the upper reproductive tract causing scarring and fibrosis that result in infertility and ectopic pregnancies. Similarly, systemic sclerosis (scleroderma or SSc) is a rheumatologic illness characterized by progressive scarring and fibrosis of the skin and visceral organs.

Fibrosis is a major contributor to scarring and infertility caused by *Chlamydia* infection, as well as the disease manifestations of systemic sclerosis (SSc). It is conventionally known that T cells, and specifically CD8 T cells, are the predominant inflammatory infiltrate in affected tissue and are thought to produce cytokines that drive the synthesis of extracellular matrix proteins by fibroblasts, resulting in excess fibrosis. Research in the mouse model for *Chlamydia* genital tract infections has shown unambiguously that scarring and infertility are mediated by CD8 T cells. Perhaps more specifically, the inventor hereof has shown in the mouse model that the CD8 T cell response to *Chlamydia* genital tract infections is atypical and includes antigen-specific CD8 T cells that produce IL-13 and tumor necrosis factor alpha (TNF-alpha) when activated; hence forth referred to herein as CD8IL-13 T cells. Similarly, in SSc, progressive scarring and fibrosis have been attributed to CD8IL-13 T cells (Fushiotti et al, 2009, Arthritis Rheum 60: 1119-28). For example, patients with SSc have enhanced numbers of CD8 T cells that produce IL-13 when activated and T cells producing IL-13 are visible in SSc skin lesions. Furthermore, activated CD8 T cells from SSc patients cause human dermal fibroblasts to express collagen and fibrinogen. The SSc CD8 T cell-driven dermal fibroblast product of scarring proteins is blocked by neutralization of IL-13, thereby directly tying the CD8IL-13 T cell subset to the immunopathology underlying SSc (Fuschiotti et al, 2013, Arthritis Rheum 65: 236-46).

Although human CD8+ T cells expressing IL-13 have been described in humans, they unfortunately do not represent a usable tool to study the biology, protein and gene expression in these cells, or to screen prospective therapeutics. This is in large part because the available human CD8IL-13 T cell subset biomarkers do not allow for the practicable purification of CD8IL-13 T cells as is required to perform the genomic and functional studies needed to develop improved diagnostic tests, test therapeutic drugs, and identify new therapeutic targets.

Accordingly, and especially given the huge impact that both *Chlamydia* infections and SSc have on human health and the problems that exist with currently available treatments for both conditions, there is a pressing need for an increased understanding of the role and of CD8 T cells in the human immune system and, more specifically, for a useful tool to study CD8IL-13 T cells. Similarly, a need exists to identify viable biomarkers for human CD8IL-13 T cells, with such biomarkers capable of practicable purification such that genomic and functional studies may be performed thereon. In this manner, meaningful diagnostic testing and therapeutic interventions could be screened for the purposes of (a) vaccine development, (b) diagnosing and treating pathological scarring during *Chlamydia*-infections, and (c) diagnosing and treating pathological scarring in patients with SSc. As provided herein, gene expression microarray experiments utilizing murine CD8IL-13 and conventional CD8 T cell clones have been used to identify candidate biomarkers for human CD8IL-13 T cells. The inventor of this application has identified that the human homolog (C10orf128) of the murine cell surface biomarker for CD8IL-13 T cells (1810011H11Rik) is expressed in the circulating CD8 T cell pool of patients with SSc and can be practicably used to purify the desired T cell subset from the peripheral blood of human subjects.

BRIEF SUMMARY

The present disclosure provides an isolated CD8+ T cell line expressing IL-13 and methods of isolating CD8+ T cells. Also provided are *Chlamydia*-specific CD8+ T cells and methods of identifying a subset of CD8 T cells that make IL-13 upon activation.

Also provided are methods for identifying and purifying CD8 T cells which express elevated levels of at least one biomarker selected from 1810011H11Rik, C10orf128, Amelx, Dclk3, Mtmr7, Arnt1, Sulf2, Pr2c5, CCR8, and Hpgds. In certain embodiments, the methods include the steps of collecting immune splenocytes from a mammal and providing at least one antigen to a *Chlamydia*-specific bacteria, and expanding and depleting the CD4+ T cell population.

In at least one exemplary embodiment of method for purifying a subset of CD8 T cells that make interleukin-13 (IL-13) upon activation, the method comprises the steps of (a) marking the CD8+ T cells by labeling CD8 or selectively removing all cell types other than CD8+ T cells to isolate the CD8+ T cells, and (b) purifying a subset of CD8+ T cells that make interleukin-13 upon activation by marking one biomarker selected from a group consisting of 1810011H11Rik, Amelx, Dclk3, Mtmr7, Arnt1, Sulf2, Pr2c5, Hpgds, CCR8, and C10orf128. Such CD8 T cells may be obtained from human blood or otherwise.

The method may further comprise the step of cloning the purified CD8+ T cells that make IL-13 upon activation. Additionally or alternatively, the method may further comprise the step of activating the CD8 T cells. In at least one embodiment, activation may be achieved with inactivated *C. muridarum* or elementary body depleted soluble antigen. In another embodiment, the method may further comprise the step of activating mononuclear cells or the isolated CD8 T cells with a phorbol 12-myristate 13-acetate+ionophore prior to purifying CD8IL-13 T cells and the step of purifying the CD8+ T cells that make IL-13 upon activation.

In at least one embodiment, the step of purifying a subset of CD8+ T cells comprises labeling the CD8 cells with at least one antibody. The antibody may be delivered via an antiserum or through any other means as is known in the art. In at least one embodiment, the at least one antibody comprises an antibody related to a cell surface domain of biomarker C10orf128. Perhaps more specifically, in at least one exemplary embodiment, the antibody is made against the peptide sequence comprising QVLATGKTPGAEID-FKY, or a functional equivalent, variant or fragment thereof. Still further, the peptide may comprise an additional cysteine or other coupling component and be linked with a carrier protein.

An additional exemplary embodiment of the present disclosure comprises a method of identifying a subset of CD8 T cells that produce IL-13 upon activation, the method comprising the steps of: obtaining a sample of cells containing CD8 T cells; measuring a gene expression in the sample of cells; determining whether the CD8 T cells in the sample express elevated levels of at least one biomarker as compared to a defined standard, the at least one biomarker selected from the set consisting of 1810011H11Rik, Amelx, Dclk3, Mtmr7, Arntl, Sulf2, Pr2c5, Hpgds, CCR8, and C10orf128; and isolating a subset of CD8 T cells that express elevated levels of the at least one biomarker from the sample.

In at least one alternative embodiment of such method, the steps of determining whether the CD8 T cells in the sample express elevated levels of at least one biomarker and isolating a subset of CD8 T cells that express elevated levels of the at least one biomarker from the sample further comprise using an anti-C10orf128 antiserum to identify the CD8 T cells. There, the anti-C10orf128 antiserum may be made against a peptide having an amino acid sequence comprising QVLATGKTPGAEIDFKY, or a functional equivalent, variant or fragment thereof, attached to a carrier protein. In at least one embodiment, the carrier protein comprises keyhole limpet hemocyanin.

Furthermore, the step of isolating a subset of CD8 T cells that express elevated levels of the at least one biomarker may further comprise depleting the CD4+ T cells present in the sample, or selectively removing all cell types other than CD8 T cells present in the sample. Additionally or alternatively, the step of determining whether the CD8 T cells in the sample express elevated levels of at least one biomarker may be applicable to the diagnosis and/or treatment of one or more disease states. For example, in at least one embodiment, the disease state(s) may comprise scarring associated with a *Chlamydia* infection or systemic sclerosis.

Formulations of an antibody are also described herein. In at least one exemplary embodiment of the present disclosure, a formulation is provided comprising a C10orf128 antibody, wherein the C10orf128 antibody is made against the peptide sequence QVLATGKTPGAEIDFKY, or a functional equivalent, variant or fragment thereof. Such antibody may, in one embodiment, comprise a monoclonal antibody. In certain embodiments, the monoclonal antibody may comprise a naked monoclonal antibody or a conjugated monoclonal antibody. Still further, certain embodiments of the present disclosure comprise an antiserum comprising an embodiment of at least one of the aforementioned antibodies.

BRIEF DESCRIPTION OF THE SEQUENCE LISTING

SEQ ID NO. 1 is a human CD8IL-13-specific peptide which, according to the subject disclosure, is related to and capable of binding the cell surface domain of the CD8IL-13 biomarker C10orf128.

BRIEF DESCRIPTION OF THE DRAWINGS

The present invention will be better understood and features, aspects and advantages other than those set forth above will become apparent in light of the following detailed description thereof. Such detailed description makes reference to the following drawings, wherein:

FIG. 5 shows that T cell culture methodologies based on irradiated naïve antigen-presenting cells (splenocytes) pulsed with UV-inactivated *Chlamydia* select out only CD4 T cells in vitro; and FIG. 6 shows biomarkers for unactivated mouse CD8IL-13 T cells. T cell clones at the end of their culture cycle were cultured for 3 additional days in medium supplemented with recombinant mouse IL-7 (3 ng/ml); total RNA was harvested from conventional CD8 T cell clones (8uvmo-2, 8uvmo-3, and a alloreactive CD8 T cells clone designated CD8bm1) and CD8IL-13 T cell clones 8sAg-1 and 8sAg-3 for comparison. Experiment was repeated three times for CD8IL-13 T cell clones 8sAg-1 & 8sAg-3; four times for the controls (8uvmo-2, 8uvmo-3, CD8bm1). Gene expression patterns were compared using the Affymetrix Mouse Gene 1.0 ST microarray; and FIG. 7 lists biomarkers unique to the CD8IL-13 T cell clones 8sAg-1 and 8sAg-3 with gene annotation; and FIG. 8 shows biomarkers for activated mouse CD8IL-13 T cells. CD8 T cell clones at the end of their culture cycle were activated overnight with immobilized anti-CD3 antibody in usual medium; 14 h later total RNA was harvested from the conventional CD8 T cell clones (8uvmo-2, 8uvmo-3, and a alloreactive CD8 T cells clone designated CD8bm1) and CD8IL-13 T cell clones 8sAg-1 and 8sAg-3 for comparison. Experiment was repeated four times for each clone. Gene expression patterns were compared using the Affymetrix Mouse Gene 1.0 ST microarray. Genes designated activated CD8IL-13 biomarkers had to be enhanced at least 3-fold with p values <0.01 for all three comparisons; *Chlamydia*-specific CD8 CD8IL-13+ vs *Chlamydia*-specific CD8 CD8IL-13−, CD8IL-13+ vs all others, and CD8IL-13+ vs. the alloreactive CD8 T cell clone CD8bm1.

Figure 1:
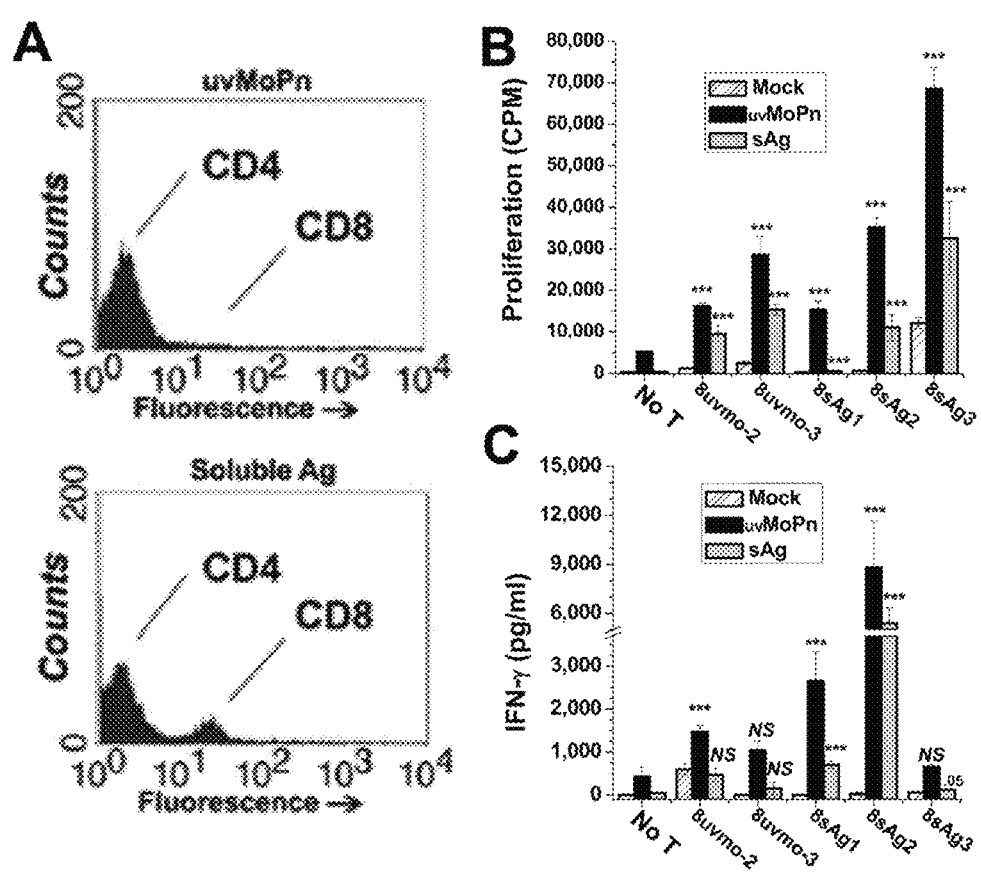
FIG. 1 shows *Chlamydia*-specific CD8 T cell clones. Subpart A) CD8 T cells are a minor subset in bulk *Chlamydia*-specific T cell populations expanded ex vivo using conventional naïve irradiated splenocytes as antigen presenting cells (<1%.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments above and claims below for interpreting the scope of the invention.

DETAILED DESCRIPTION

For the purposes of promoting an understanding of the principles of the present disclosure, reference will now be made to the embodiments illustrated in the drawings and specific language will be used to describe the same. It will nevertheless be understood that no limitation in scope of this disclosure is thereby intended. Indeed, the materials, systems, and methods of the present disclosure may be embodied in many different forms and should not be construed as being limited to the embodiments expressly set forth herein.

Likewise, many modifications and other embodiments of the materials, systems and methods set forth herein will come to mind to one of skill in the relevant arts having the benefit of teachings presented herein. Therefore, it is to be understood that any such alterations, modifications, embodiments and further applications of the principles of the present disclosure are intended to be included within the scope of the appended claims. Although specific terms may be employed herein, they are used in a generic and descriptive sense only and not for purposes of limitation.

Unless defined otherwise, all technical and scientific terms used herein have the same meaning as commonly understood by one of skill in the relevant arts. Although any methods and materials similar to or equivalent to those described herein can be used in the practice or testing of the present invention, the preferred methods and materials are described herein.

The disclosure of the present application provides for isolated *Chlamydia*-specific CD8+ T cells that express interleukin-13 (IL-13) and various methods of isolating and using the same. Specifically, certain embodiments of the CD8+ T cells and methods disclosed herein provide useful insights into *Chlamydia*-associated immunopathology. Additionally, a novel human biomarker C10orf128 (the human homolog of mouse 1810011H11Rik) and a related CD8IL-13 cell surface domain peptide for C10orf128 are disclosed. The biomarkers described herein may be used to identify and/or purify a subset of IL-13 expressing CD8 T cells. Related antibodies and antiserums are also described herein which may be used to sort C10orf128 positive CD8 T cells from human blood. Such aspects of the present disclosure are noteworthy as the methodologies and techniques described herein represent significant advances over the conventional diagnostic and therapeutic interventions currently available for patients with scleroderma or *Chlamydia* infections.

In general, CD8 T cell subsets have a role in protection and immunopathology during *Chlamydia* genital tract infections. As described in more detail below, the *Chlamydia*-specific CD8 T cells clones described herein are a minority subset in polyclonal T cell populations that were expanded in vitro from C57BL/6 mice that previously cleared *C. muridarum* genital tract infections. Because CD8 T cell response has been associated with immunopathology, it is important to understand the nature of *Chlamydia*-specific CD8 T cell responses. Cloning *Chlamydia*-specific CD8 T cells from polyclonal populations derived from immune mice reveals that the majority of CD8 T cells are not restricted by MEW class Ia molecules and have cytokine production patterns that are consistent with immunopathology (methods and materials described in further detail in Johnson et. al, 2014, Immunology January 15. doi: 10.1111/imm.12248. PMID: 24428415, which is hereby incorporated herein by reference in its entirety). While cytokine patterns provide a link to immunopathology, some of these CD8 T cell clones are able to control *C. muridarum* replication in reproductive tract epithelial cells in vitro. Accordingly, all mechanisms of clearance are not equal. Information gleaned from these novel CD8 T cell clones correlates with the CD8 T cells' role in immunopathogenesis in vivo.

Because *Chlamydia* species are intracellular pathogens, early efforts to understand protective immunity focused on CD8 T cells, including isolation and characterization of CD8 T cell clones that were protective against infection (Igiesteme et. al, 1994, Infect Immun 62:5195-5197). However the importance of CD8 T cells to protective immunity was brought into question by depletion studies and knockout mice. Indeed, it was shown that CD8-depleted and beta 2 microglobulin knockout mice were not compromised in their ability to clear *C. muridarum* genital tract infections (Morrison et. al. 1995, Infect Immun 63:4661-4668). In parallel, human studies with *Chlamydia*-specific CD8 T cell clones isolated from infected individuals showed that the majority of the T cells clones were not restricted by classical or non-classical MHC class I molecules (Gervassi et. al, 2003, J Immunol 171:4278-4286 and Matyszak et. al, 2004, Infect Immun 72:4357-4367).

More recent studies in the *C. muridarum* mouse model have implicated CD8 T cells in immunopathology and infertility (Igietseme et al., 2009, J Infect Dis 200:926-934). Research has shown that immune responses mediated by CD8 T cells are major contributors to the pathology of *Chlamydia*. Additionally, tumor necrosis factor alpha (TNF-α) was found to be critical for CD8 T cell mediated immunopathology (Murthy et al., 2011, Infect Immun 79:2928-2935).

The identity of the CD8 T cell subset(s) mediating immunopathology during genital tract infections is not well understood in mouse or man. To address this issue *Chlamydia*-specific CD8 T cell clones were isolated from mice that had previously cleared *C. muridarum* genital tract infections and investigated their immunobiology including restriction elements, cytokine patterns and the ability to terminate *Chlamydia* replication in upper reproductive tract epithelial cells.

EXAMPLES

Materials and Methods
Mice
4-5 week old female C57BL/6 mice from Harlan Labs (Indianapolis, Ind.) and $K^bD^b$ double knockout female mice (lack MHC class Ia molecules) from Taconic (Hudson, N.Y.) were used. All mice were housed in a pathogen-free barrier animal facility.

Epithelial Cells and Bacteria.
C57epi.1 epithelial cells and McCoy fibroblasts were cultured. *Mycoplasma*-free *Chlamydia* muridarum (Nigg), previously known as *C. trachomatis* strain mouse pneumonitis (MoPn) (Nigg) was grown in McCoy cells. Elementary body (EB)-depleted *Chlamydia* antigen was prepared by infecting 175 $cm^2$ flasks of McCoy cells with *C. muridarum* at 3 IFU per cell. 32 h post infection the monolayers were removed using sterile glass beads, sonicated 60 sec, spun at low speed (464 g×10 min) to remove debris, then centrifuged 19,000 g×30 min to pellet elementary bodies (EB); ~99.998% depletion. EB-depleted supernatants were collected, concentrated (4000 g×30 min) in ultrafiltration centrifuge units with 30 kd MW cut off (Amicon Ultra-15; Millipore, Billerica Mass.), aliquoted and stored at −80° C.

Genital Tract Infections.
One week prior to infection, mice were treated with 2.5 mg of medroxyprogesterone delivered subcutaneously (Depo-Provera, Pfizer Pharmaceuticals, New York, N.Y.). Lightly anesthetized C57BL/6 female mice were infected vaginally with $5\times10^4$ inclusion forming units (IFU) of *C. muridarum* (Nigg) in 10 μl of SPG buffer. Mice were swabbed 7 days post infection and IFU quantified to document infection. Mice >6 weeks post infection were considered immune mice.

While in the foregoing embodiment the mice were artificially infected with the bacteria, a mammal with a naturally acquired infection could alternatively be used to derive the CD8 T cell clones. In such case, the CD8 T cell clones can be derived pursuant to the methods described herein after the infection has been given a sufficient time to allow for a T cell immune response in the infected mammal (typically longer than about two weeks).

*Chlamydia*-Specific CD8 T Cells.
After bacterial clearance, CD8 T cell clones were derived from immune splenocytes after expansion on irradiated immune splenocytes (novel approach) and *Chlamydia* antigen, and depletion of CD4 T cells, by limiting dilutions using either UV-inactivated *C. muridarum* (*mycoplasma*-free *Chlamydia muridarum* (Nigg) (MoPn)) or elementary body (EB)-depleted soluble *C. muridarum* antigen preparations as the stimulus (about 99.998% depletion of EB by centrifugation) as described in further detail below. (Johnson et. al, 2014, Immunology January 15. doi: 10.1111/imm.12248. PMID: 24428415).

T cell expansion cultures were performed in RPMI 1640-25 mM HEPES supplemented with 10% characterized fetal bovine serum (HyClone), 2 mM Lalanyl-L-glutamine (Glutamax I; Gibco/Invitrogen), 25 μg/ml gentamicin (Sigma), and $5\times10^{-5}$ M 2-mercaptoethanol (Sigma; St. Louis, Mo.); referred to as RPMI CM. Immune splenocytes harvested from mice were plated at 12.5×106 cells per well in tissue culture treated 12 well plates, in RPMI CM containing murine recombinant IL-1α (2 q g/ml), IL-6 (2 ηg/ml), IL-7 (3 ηg/ml), IL-15 (4 ηg/ml), human recombinant IL-2 (100 units/ml) (Chiron Corp.; Emeryville Calif.), 20% 2° mixed lymphocyte culture supernatant, and 20 μl per well EB-depleted *C. muridarum* antigen. Subsequent passages in 24 well plates used $2.5\times10^5$ T cells and $5\times10^5$-γ-irradiated (1200 rad) immune splenocytes APC and the same conditions as in the primary culture. CD4 T cells were depleted from polyclonal populations by magnetic bead separation per the manufacturer's protocol (Miltenyi Biotec; Auburn Calif.). The resulting polyclonal CD8 T cell populations were cloned by limiting dilution and passed weekly as above. Recombinant mouse cytokines were purchased from R&D Systems (Minneapolis, Minn.).

Flow Cytometry.
T cell clones were stained for 20 min on ice in RPMI CM with: Unconjugated 145-2c11 (CD3), FITC-coupled PE-coupled 53-5.8 (CD8β), PE-coupled 53-6.7 (CD8α) (BD Biosciences; San Jose Calif.), PE-coupled YTS191.1 (CD4) (Cedarlane Laboratories; Burlington, N.C.), FITC-coupled Mouse IgG2a (control antibody), PE-coupled Rat IgG2b (control antibody) (Ebioscience; San Diego, Calif.), FITC-coupled Goat anti-Armenian Hamster Ig (Jackson Immunoresearch Laboratories; West Grove Pa.). Cells were fixed with 1% paraformaldehyde after staining and subsequently analyzed on a FACSCalibur cytometer (BD Biosciences).

T Cell Proliferation Assays.

$2.5 \times 10^5$ T cells were added to $2.5 \times 10^5$ γ-irradiated immune splenocytes (2000 rad) with antigen (UV-*C. muridarum* or sAg) and without (sucrose phosphate glutamate buffer; SPG) in 96 well u-bottom plates; wells pulsed with 0.5 µCi/well $^3$H-thymidine (ICN, Costa Mesa, Calif.) for 12 h at 36-48 h of the culture cycle. $^3$H-thymidine incorporation was measured with a TopCount beta counter.

T Cell Cytokine ELISAs.

For the specificity experiment in FIG. 12, the conditions were the same as for the proliferation assay detailed above. For the MHC mapping experiments (FIG. 13), the conditions were the same except immune and naïve splenocytes were more lightly irradiated with 1000 rad (better antigen presentation capabilities) and all wells contained 1 ng/ml recombinant IL-7 to support T cell viability over the 72 h experiment. For cytokine polarization determination, T cells were activated by immobilized anti-CD3 antibody (145-2C11; NA/LE BD Pharmingen, San Jose, Calif.). Flat-bottom 96 well tissue culture plates were prepared by incubating 50 µl of 0.5 µg/ml 145-2C11 in PBS overnight at 4° C. Wells were washed once with media prior to use. $5 \times 10^4$ T cells were added to each well and supernatants collected at 24 h. Relative levels of IL-2, IL-10, IL-13, IL-17, IFN-γ, and TNFα determined by ELISA using capture and biotinylated monoclonal antibody pairs with recombinant murine standards according to the manufacturer's protocols: IL-2 ELISA: 1A12 and 5H4, IFN-γ: XMG1.2 (Thermo Scientific; Rockford, Ill.); TNFα: TN3-19.12/C1150-14; IL-10: JES5-2A5/SXC-1 (BD Biosciences; San Jose, Calif.); IL-13: Ebio13a/Ebio1316H (Eboscience; San Diego, Calif.). Recombinant murine IL-2, IL-10 (Thermo Scientific), IFN-γ (R&D Systems; Minneapolis, Minn.), IL-13 (Ebioscience) and IL-17a (Biolegend; San Diego, Calif.) were used as standards. Detection was accomplished with Streptavidin-HRP (BD Biosciences) and TMB substrate (Sigma).

*Chlamydia* Replication Experiments.

C57epi.1 cell monolayers in 48-well plates were untreated or treated with IFN-γ (10 ηg/ml) for 14 h preinfection. Wells were infected with 3 inclusion forming units (IFU)/cell. After addition of *C. muridarum*, the plates were spun at 1200 rpm (300×g) for 30 min. Mock-infected wells received an equivalent volume of sucrose-phosphate-glutamate acid buffer lacking *C. muridarum*. Four hours post infection, the inoculums were removed and $1.5 \times 10^5$ CD4 T cell clone cells were added per well. Twenty eight hours later, 32 h post infection, wells were scraped, harvested in sucrose phosphate buffer (SPG), and stored at –80° C. until titers could be determined on McCoy cell monolayers.

Gene Expression Microarray Analysis

T cell clones 8uvmo-2, 8uvmo-3, sAg-1, sAg-3 and CD8bm1 were purified by ficoll-hypaque (histopaque 1083; Sigma Chemical Co.) at the end of their culture cycle and then grown for 3 days in RPMI CM supplemented with 3 ng/ml recombinant mouse IL-7 without antigen stimulation (resting state) or activated for 14 h with immobilized anti-CD3 antibody (as in T cell cytokine methods) in RPMI CM (activated state). Total RNA was isolated from each T cell clone using a protocol that included an RNAse-free DNAse I treatment step (RNAeasy; Qiagen, Valencia, Calif.). With assistance from the Indiana University Center for Medical Genomics, gene expression patterns were analyzed using the Affymetrix Mouse ST 1.0 Array that analyzes 28,853 murine genes. Samples were labeled using the standard Affymetrix protocol for the WT Target Labeling and Control Reagents kit according to the Affymetrix user manual: GeneChip® Whole Transcript (WT) Sense Target Labeling Assay GeneChip. Individual labeled samples were hybridized to the Mouse Gene 1.0 ST GeneChips® for 17 hours then washed, stained and scanned with the standard protocol using Affymetrix GCOS (GeneChip® Operating System). GCOS was used to generate data (CEL files). Arrays were visually scanned for abnormalities or defects. CEL files were imported into Partek Genomics Suite (Partek, Inc., St. Louis, Mo.). RMA signals were generated for the core probe sets using the RMA background correction, quantile normalization and summarization by Median Polish. Summarized signals for each probe set were log 2 transformed. These log transformed signals were used for Principal Components Analysis, hierarchical clustering, and signal histograms to determine if there were any outlier arrays. Untransformed RMA signals were used for fold change calculations.

Data was analyzed using a 1-way Anova (analysis of variance) using log 2 transformed signals for all four CD4 T cell clones, and contrasts were made comparing iNOS-dependent uvmo-4 and sp114-10 individually to the combined expression of the iNOS-independent T cell clones uvmo-2 and uvmo-3. Fold changes were calculated using the untransformed RMA signals. Genes up or down regulated 5-fold with p values <0.001 for either uvmo-4 or sp14-10 compared to uvmo-2/uvmo-3 were considered in the final analysis (supplemental table 1). The microarray data presented herein is available in the Gene Expression Omnibus database under accession number GSE32128.

RT-PCR.

After IRB approval, peripheral blood CD8 T cell clones were purified from the peripheral blood of healthy human subjects (three), human subjects with systemic sclerosis (two), human subjects with acute *Chlamydia* infections (three), and one individual with a necrotizing granulomatous process of unclear etiology. The mononuclear fraction of blood was isolated utilizing Lymphoprep tubes. The mononuclear fraction from each subject was incubated for 40 minutes in 2 wells of a tissue culture-treated plastic 6 well plate. Non-adherent cells were collected and "untouched" CD8 T cells isolated using a commercial magnetic bead kit (Miltenyi Biotech).

Figure 9:
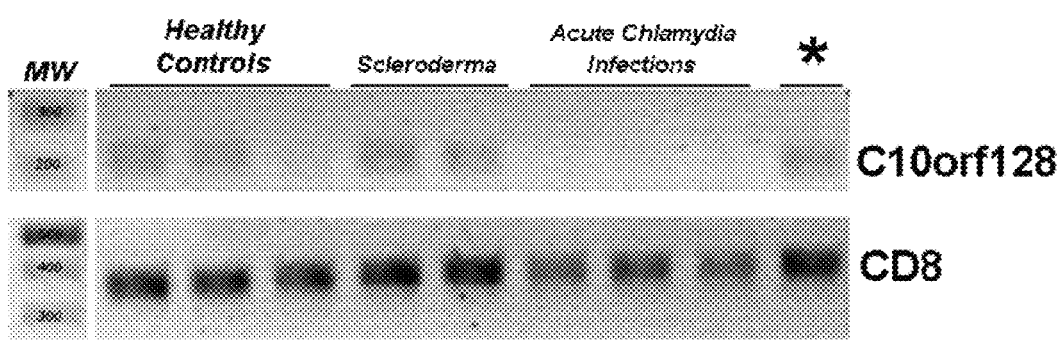
FIG. 9 shows expression of C10orf128 in CD8 T cells purified from the peripheral blood of human subjects. Human subjects were divided into four groups: healthy controls; scleroderma; acute *Chlamydia* infection; necrotizing lymphadenitis of unknown etiology. Total RNA was isolated from the purified CD8 T cell pools and subjected to RT-PCR with primers for C10orf128 (human homolog of mouse CD8IL-13 biomarker 1810011H11Rik) and CD8 (loading control). Patients with scleroderma had equal to or greater C10orf128 mRNA in their circulating CD8 T cell pool than all other subjects in spite of treatment with mycophenolate (a therapeutic toxin affecting activated lymphocytes)
Figure 10:
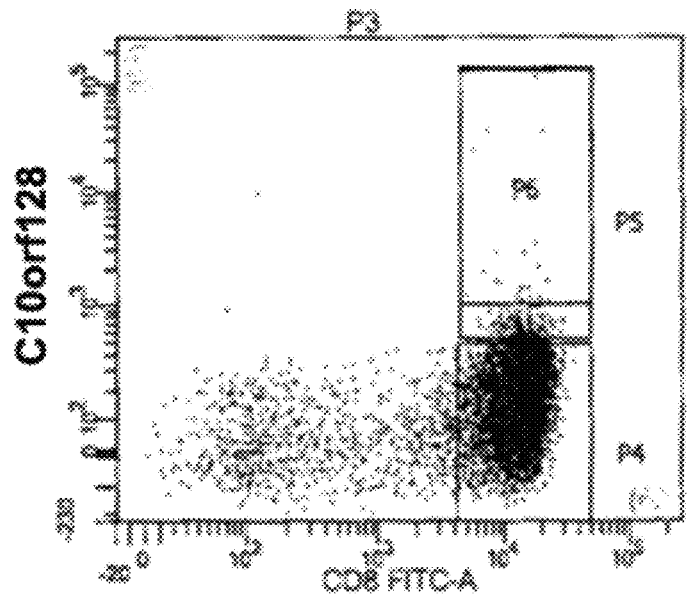
FIG. 10 shows C10orf128 positive CD8 T cells are ~0.2% of the circulating CD8 T cell pool in a healthy individual (gate P6). Conclusion: There are sufficient C10orf128+ (e.g., CD8IL-13) T cells circulating in the peripheral blood of a healthy person to do practicable isolation for functional and molecular studies. Extrapolating from the results shown in FIG. 9, there should also be sufficient C10orf128+CD8 T cells in the peripheral blood of individuals with systemic sclerosis to do practicable isolation of C10orf128+CD8 T cells for functional and molecular studies.

Total RNA was isolated from each subject's purified T cells using a protocol that included an RNase-free DNase I treatment step (RNAeasy; Qiagen, Valencia, Calif.). Specific mRNA gene reverse transcription and amplification were performed using AMV reverse transcriptase/Tfl DNA polymerase in a onestep system (AccessQuick RT-PCR; Promega, Madison, Wis.). Amplification conditions were 1) 48° C. for 45 min; 2) 95° C. for 2 min; 3) 95° C. for 30 s; 4) 57° C. for 20 s; 5) 72° C. for 30 s; 6) go to step 3 for X times; 7) 72° C. for 7 min; and 8) hold at 4° C. using an MJ Research J200 PCR machine. 250 ng of total RNA with 40 cycles was used for the CD8 (loading controls; expected PCR product 356 base pairs); 500 ng of total RNA with 42 cycles was used for the C10orf128. PCR reactions lacking reverse transcriptase (DNA contamination controls) for CD8 and C10orf128 reactions showed no PCR products (data not shown). Primer pairs used were CD8 (ccagtcccaccttcctc-ctatac, gatatcacaggcgaagtccagc; PCR product 356 base pairs) and C10orf128 (atgaacttggggtcagcatgct, agagtcgtcgtcaaataagtgcctc; PCR product 204 base pairs)

sense and antisense primers using a one-step RT-PCR reagent (Access RT-PCR, Promega). Products of the RT-PCR reactions were separated on 2.5% agarose gels containing ethidium bromide (FIG. 9). Images of the gels were inverted for presentation purposes.

Cell Sorting.

After IRB approval, 30 cc of blood was taken from a healthy human volunteer. The mononuclear fraction was isolated with Lymphoprep tubes, incubated in media for 40 minutes at 37° C., and "untouched" CD8 T cells were purified using a Miltenyi Biotech magnetic bead kit. The purified viable CD8 T cells were stained with the exemplary rabbit antiserum of the present disclosure that is, in at least one embodiment, specific for C10orf128, for CD8, and with a violet live/dead dye. Cells were sorted on a FACS Aria III isolating viable C10orf128 positive CD8 T cells and C10orf128 negative T cells as internal controls.

Statistical Analysis.

Summary figures for each experimental investigation are presented as 'pooled' means and with their associated standard error of the mean (SEM). Figure legends indicate the number of independent experiments pooled to generate each figure. Student's two-tailed t-tests and Wilcoxon non-parametric tests, depending on data distribution, were used to assess significance of experimental data. Homogeneity of variances was assessed using a folded F-test. All data were verified to meet analytic assumptions. Analyses were performed using SAS 9.3 (SAS Institute, Cary, N.C.). p values <0.05 were considered statistically significant.

Example 1. *Chlamydia*-Specific T Cell Clones

Figure 5:
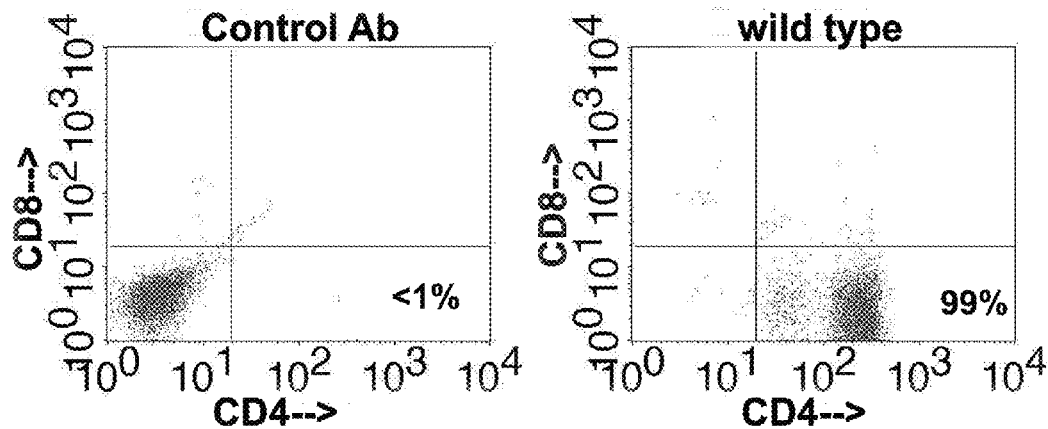
FIG. 5); however, using immune irradiated splenocytes with either UV-inactivated *C. muridarum* (uvMoPn) or soluble antigen (soluble Ag) allowed expansion of *Chlamydia*-specific CD8 T cells. Soluble antigen was more effective than uvMoPn for CD8 T cell expansion. Subpart B) Specificity of five CD8 T cell clones derived using irradiated immune splenocytes as feeder APC. Each T cell clone was activated with irradiated (2000 rad) immune splenocytes mock-pulsed, uvMoPn-pulsed, and EB-depleted antigen (sAg)-pulsed. At 36 h culture supernatants were harvested and 3H-thymidine added; wells were harvested at 48 h to score proliferation. Proliferation shown in counts per minute (CPM). Subpart C) IFN-γ production as determined by ELISA. Data are Means and SD for one experiment done as quadruplicates. For each T cell clone the experimental wells were compared to its mock-pulsed control and to the APC only control (No T) for the relevant antigen. The higher p value of those two comparisons (the least significant) was assigned and graphed. *=p value <0.05; =p value <0.005; *=p value <0.0005. Conclusion: All CD8 T cell clones recognized antigen-pulsed immune splenocytes as measured by proliferation, IFN-γ production, or both.

To better understand *Chlamydia* pathogenesis, *Chlamydia*-specific T cell clones were derived from immune mice using UV-inactivated-*C. muridarum*-pulsed naïve splenocytes as antigen presenting cells (APC) (Jayarapu et al. 2009, Infect Immuno 77:4469-4479). Under those conditions, polyclonal T cell cultures were about 100% CD4 T cells (see FIG. 5). Isolating *Chlamydia*-specific CD8 T cells clones from mice was performed in order to study their immunobiology and compare them with *Chlamydia*-specific CD8 T cells that have been described in humans. An alternative culture system based on immune Ig-receptor-bearing APC may utilize cross-presentation pathways to generate more CD8 T cell epitopes and promote greater expansion of CD8 T cells. Activating lymphocytes from immune mice with immune-irradiated splenocytes pulsed with either UV-*C. muridarum* (uvMoPn) or the EB-depleted-infected-epithelial-cell lysates (soluble *Chlamydia* antigens (sAg)) yielded polyclonal T cell populations with small, but readily detectable, CD8 T cell populations (see FIG. 1, subparts A-C).

Immune-irradiated splenocytes pulsed with UV-inactivated-*C. muridarum* expanded a small, but detectable, CD8 T cell population (~3%), while those immune-irradiated splenocytes pulsed with sAg expanded a bit larger of a detectable CD8 T cell population (~10%) (subpart A of FIG. 1). CD4 T cells were selectively depleted from both of those polyclonal populations using magnetic bead technology, and the remaining T cell populations cloned by limiting dilution to derive two "UV-*C. muridarum*" CD8 T cell clones (labeled in the Figure as "8uvmo-1" and "8uvmo-2") and three "soluble antigen" CD8 T cell clones (which are labeled in the Figure as "8sAg-1," "8sAg-2" and "8sAg-3"). Accordingly, CD8 clones from 2 mice were isolated by limiting dilution after CD4 T cell depletion from polyclonal populations by magnetic bead separation. The resulting five *Chlamydia*-specific CD8 clones specifically recognized infected C57BL/6 oviduct epithelial cells over uninfected controls (subpart C of FIG. 4) and recognized UV *C. muridarum*-pulsed immune syngeneic splenocytes (subparts B and C of FIG. 1).

As shown herein (see Example 5 below), conventional MHC class Ia-restricted *Chlamydia*-specific CD8 T cells are not the dominant CD8 T cell type in *Chlamydia*-specific T cell populations expanded from immune mice. Indeed, the majority of the *Chlamydia*-specific CD8 T cell clones are not restricted by MHC class Ia molecules (see FIG. 2). Specifically, three of the five CD8 T cell clones (8sAg-1, -2, -3) were activated as well or better by Balb/c and MHC class Ia deficient naïve splenocytes pulsed with uvMoPn as compared to those derived from syngeneic naïve C57BL/6 pulsed with uvMoPn. Furthermore, two atypical *Chlamydia*-specific CD8 T cells exhibited an unusual cytokine polarization that included combinations of IFN-γ, TNF-α, IL-10, and IL-13 (FIG. 3), representing the successful application of the methodology described herein.

Figure 3:
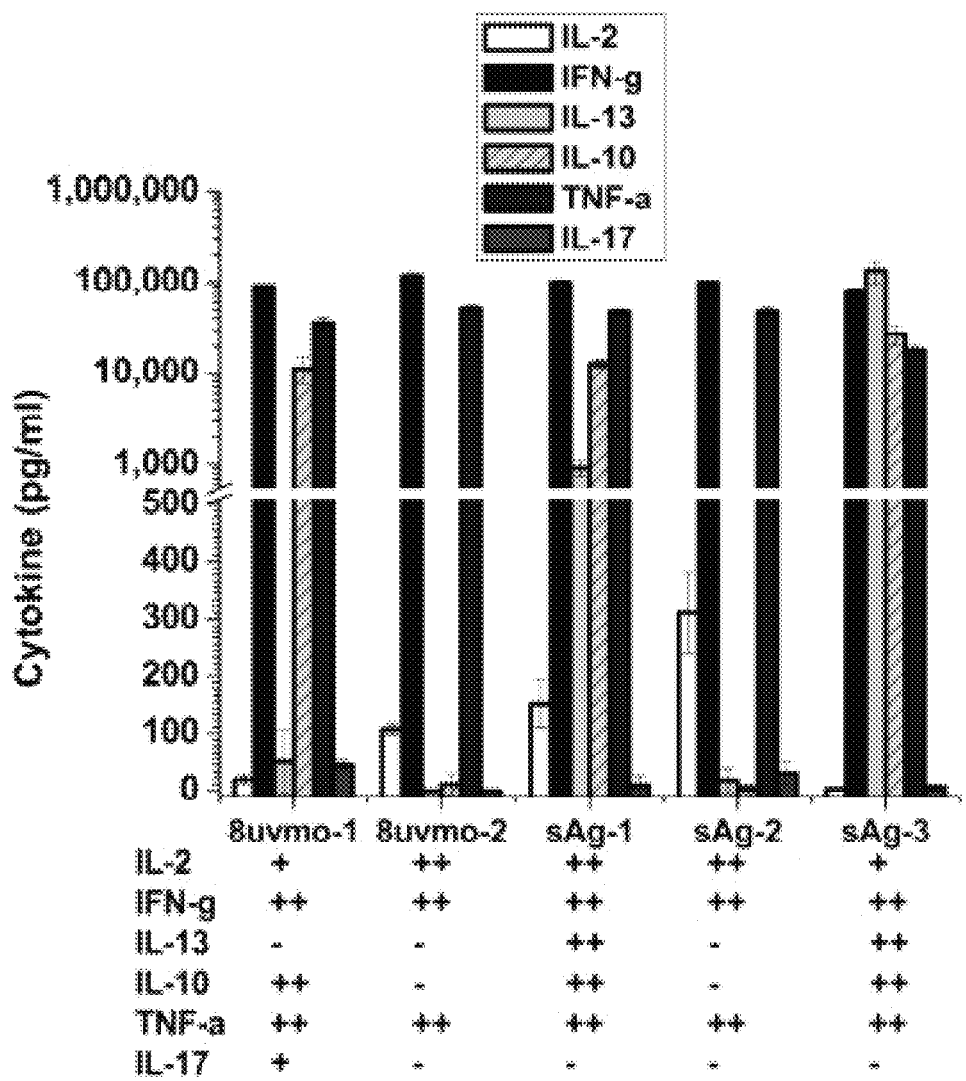
FIG. 3 shows cytokine patterns in CD8 T cell clones. The CD8 T cell clones were activated with immobilized anti-CD3 antibody. Supernatants were collected at 24 h and indicated cytokine patterns determined by ELISA. Aggregate data from two independent experiments shown.

Here, the CD8 T cell clones had varying abilities to terminate *Chlamydia* replication in epithelial cells (see FIG. 4, subparts A-C). 8uvmo-2 and 8uvmo-3 were effective in terminating *C. muridarum* replication; however, 8sAg-1, 8sAg-2, and 8sAg-3 were unable or inefficient at terminating replication even when the epithelial monolayers were pretreated with IFN-γ. Finally and summarily, as illustrated in FIG. 3, two of the five CD8 T cell clones produced large amounts of IL-13 in addition to IL-2, TNF-α, IL-10, and IFN-γ.

IL-13 producing *Chlamydia*-specific CD8 T cells may contribute to immunopathology during *C. muridarum* genital tract infections based on the roles of TNF-α and IL-13 in scar formation. Specifically, data shows that TNF-α is associated with immunopathology (Murthy et al., 2011, Infect Immun 79: 2928-35) and IL-13 is detrimental to *Chlamydia* clearance and associated with fibrosis and residual scarring (Asquith et al., 2013, Plos Path 7:e1001339). CD8 T cells producing IL-10, IL-13 and TNF-α are interesting with respect to immunopathology because in addition to a role for IL-10 in scarring, the combination of TNF-α and IL-13 is the underlying mechanism for bleomycin-induced pulmonary fibrosis and TNBS-induced colonic fibrosis in mouse models (Fichtner-Feigl et al, 2006, Nat Med 12:99-106; Fichtner-Feigl et al, 2007, J Immunol 178: 5859-70). Further, IL-13 expressing CD8 T cells may mediate immunopathology in systemic sclerosis, a rheumatologic disorder that manifests as progressive scarring of the skin, and *Chlamydia*-specific CD8 T cells making IL-10, IL-13 and TNF-α may contribute to the CD8-mediated immunopathology observed in experimental murine genital tract infections. Accordingly, the atypical CD8 T cell clones described herein are an important effector T cell subset for *Chlamydia*-associated immunopathology and representative of the atypical CD8 T cells previously described in humans (Gervassi et al., 2003, J Immunol 171:4278-86; Matyszak et al., Infect Immun 72:4357-67).

Example 2. *Chlamydia*-Specific CD8 IL-13 T Cell Clones Compared with Conventional CD8 T Cell Clones

*Chlamydia*-specific CD8 IL-13 T cell clones were compared with conventional CD8 T cell clones. CD8 T cell clones were grown under their usual culture conditions. At the end of the culture cycle the T cells were harvested and purified by ficoll-hypaque centrifugation to remove debris.

The purified T cell clones were grown under non-activating conditions with recombinant murine IL-7 for 72 hours, then total RNA harvested and analyzed with Affymetrix Mouse ST 1.0 Array as described in Johnson, R. M., M. S. Kerr, and J. E. Slaven. 2012. Plac8-dependent and inducible NO synthase-dependent mechanisms clear *Chlamydia muridarum* infections from the genital tract. J. Immunol., 188: 1896-1904. To investigate CD8IL-13 gene expression after T cell activation, the same microarray experiment previously described was repeated harvesting total RNA 14 h after activation by immobilized anti-CD3 monoclonal antibody. Gene expression microarrays were used to identify biomarkers and potential therapeutic targets in both resting and activated CD8IL-13 T cells.

Figure 8:
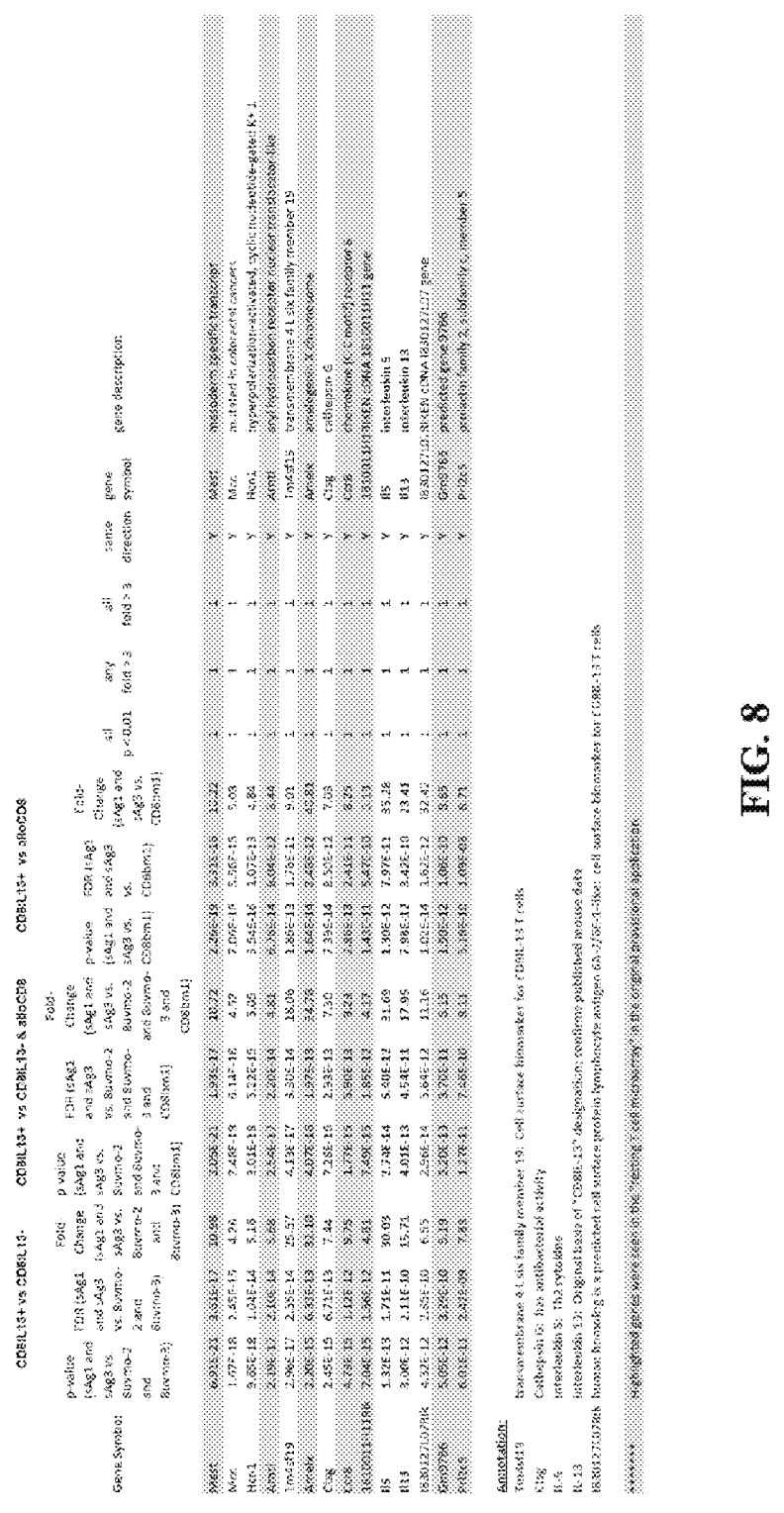

Referring to FIGS. 6-8, Affymetrix gene expression microarray comparison is shown of two *Chlamydia*-specific CD8IL-13 T cell clones versus two *Chlamydia*-specific CD8 T cell clones that do not produce IL-13 plus a conventional alloreactive CD8 T cell clone specific for H-2K$^{bm1}$ (column labeled: Fold-Change (CD8IL13+ vs. CD8IL13− and allo CD8)); comparison of two *Chlamydia*-specific CD8IL-13 T cell clones versus two *Chlamydia*-specific CD8 T cell clones that do not produce IL-13 (column labeled: Fold-Change (CD8IL13+ vs. CD8IL13−)); comparison of two *Chlamydia*-specific CD8IL-13 T cell clones versus a conventional alloreactive CD8 T cell clone specific for H-2K$^{bm1}$ (column labeled: Fold-Change (CD8IL13+ vs. allo CD8)).

Example 3. CD8IL-13 is a Subset of CD8 T Cells with Enhanced Expression of 1810011H11Rik, Amelx, Dclk3, Mtmr7, Arnt1, Sulf2, Pr2c5, CCR8 and Hpgds Activation of CD8IL-13 T cells identified unique and expected IL-13 production, unexpected IL-5 production, unique cell surface biomarkers Tm4sf19 & 1830127L07Rik, and the anti-bacterial protein cathepsin G in addition to previously identified resting CD8IL-13 biomarkers. The activated CD8IL-13 T cells had uniquely elevated mRNA for Mcc and Hcn1 whose biological significance in the T cell phenotype is unknown.

To investigate the mechanism underlying CD8 immunopathology, *Chlamydia*-specific CD8 T cell clones were isolated from mice that self-cleared genital tract infections. *Chlamydia*-specific CD8 T cell clones could not be derived with antigen-pulsed irradiated naïve splenocytes; instead derivation required use of irradiated immune splenocyte antigen presenting cells (APC). The majority of *Chlamydia*-specific CD8 T cell clones were not restricted by MHC class Ia molecules and had varying abilities to terminate *Chlamydia* replication in epithelial cells. Two of the five CD8 clones produced IL-13 in addition to IL-2, TNFα, IL-10, and IFN-γ. IL-13 producing *Chlamydia*-specific CD8 T cells may contribute to immunopathology during *C. muridarum* genital tract infections based on the roles of TNFα and IL-13 in scar formation (Fichtner-Feigl et al, 2006, Nat Med 12: 99-106).

Two *Chlamydia*-specific CD8 T cell clones were derived from immune mice infected previously with *C. muridarum* lacked MHC class Ia restriction and had cytokine polarization patterns that included TNFalpha and IL-13.

Example 4. Derivation of *Chlamydia*-Specific CD8 T Cells Required Immune Splenocyte APC Some procedures for derivation of *Chlamydia*-specific CD4 T cell clones from immune mice may be relatively routine. However those protocols based on irradiated naïve splenocytes pulsed with UV-inactivated *C. muridarum* did not expand *Chlamydia*-specific CD8 T cells. Therefore culture conditions were investigated using alternative APC feeder layers and *Chlamydia* antigens.

Splenocytes from mice that had previously self-cleared genital tract infections were harvested and stimulated in vitro with UV-inactivated *C. muridarum* or with soluble *C. muridarum* antigen prepared by depleting infected cell lysates of elementary bodies (~99.998%) by centrifugation. For the secondary stimulation and subsequent passages, the T cell populations were activated with irradiated immune splenocytes pulsed with UV-inactivated *C. muridarum* or EB-depleted antigen, as per the primary culture. Under these conditions there was significant expansion of a CD8+ T cell population (FIG. 1, subpart a). Polyclonal cultures activated with UV-inactivated *C. muridarum* had a minority CD8 T cell population of ~3%, while cultures activated with EB-depleted antigen had a minority CD8 T cell population of ~10%. Those bulk T cell populations were depleted of CD4 T cells using magnetic bead separation, then cloned by limiting dilution on irradiated immune splenocytes pulsed with the relevant antigen. Five CD8 T cell clones were kept for further study; all clones were CD3+CD8αβ T cells. Their specificity was tested by proliferation and IFN-γ production when activated by irradiated immune-splenocytes mock-pulsed or pulsed with UV-inactivated *C. muridarum* or EB-depleted *Chlamydia* antigen (FIG. 1, subparts b & c). All the clones recognized immune splenocytes pulsed with UV-inactivated *C. muridarum* or EB-depleted antigen to greater or lesser degrees. All clones recognized their original antigen by proliferation and IFN-γ production with one exception; 8uvmo-3 production of IFN-γ was not statistically greater than antigen-pulsed immune splenocytes IFN-γ production. None of the clones recognized immune splenocytes pulsed with freeze/thawed McCoy cells, ruling out cross-presentation of McCoy alloantigens (data not shown).

Example 5. Three *Chlamydia*-Specific CD8 T Cell Clones are not Restricted by MHC Class Ia Molecules In two previous independent human studies the majority of *Chlamydia*-specific CD8 T cells isolated from individuals with *C. trachomatis* genital tract infections were not restricted by HLA class Ia molecules. In that context, determining the restriction element for the five murine CD8 T cell clones was investigated.

Irradiated immune splenocytes produce cytokines capable of supporting antigen-independent proliferation and IFN-γ production, making them ill-suited for MHC restriction mapping. However, irradiated naïve splenocytes pulsed with *Chlamydia* antigens do not produce measurable cytokines and did not support meaningful antigen-independent IFN-γ production by bystander T cells.

Figure 2:
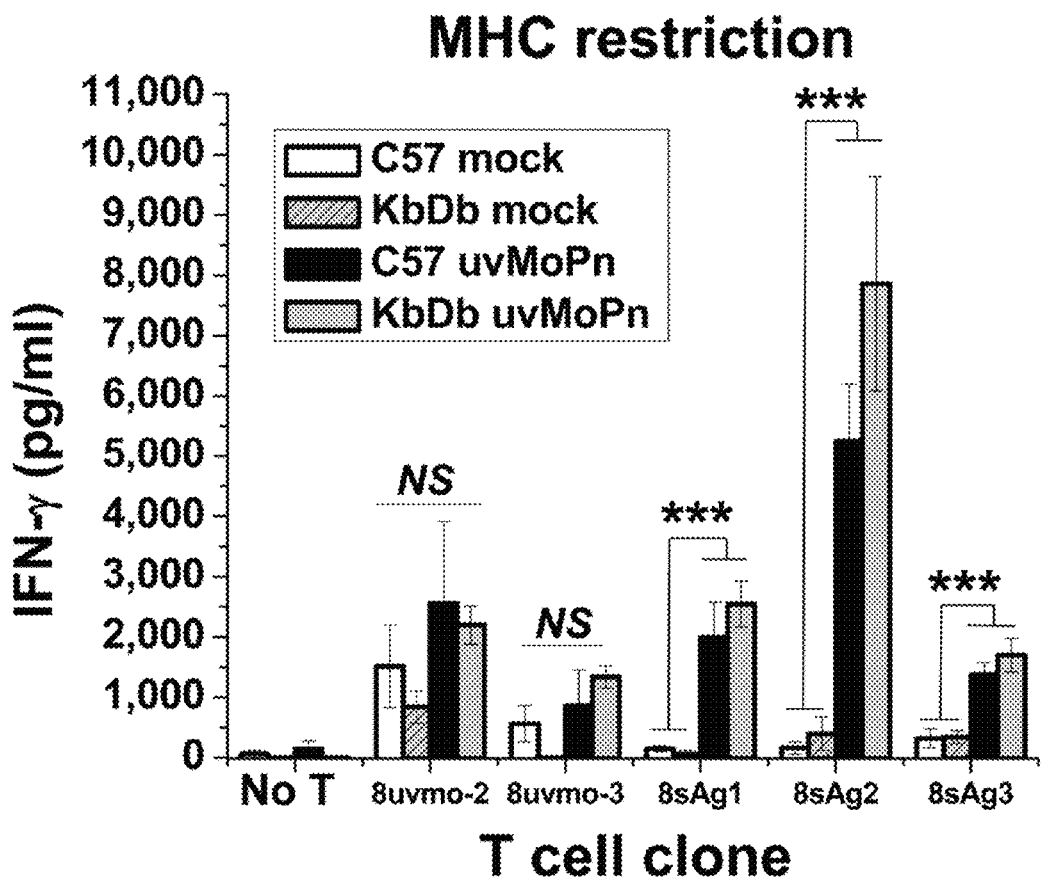
FIG. 2 shows mapping of MHC restriction elements using naïve splenocytes. CD8 T cell clones were mock-activated and uvMoPn-activated with irradiated (1000 rad) naïve C57BL/6 and KbDb knockout mouse splenocyte APC. Supernatants were collected at 72 h and levels of IFN-γ determined by ELISA. Data presented are aggregate data from two independent experiments. *=p value <0.05; =p value <0.005; *=p value <0.0005. Conclusion: Three of the five CD8 T cell clones (8sAg-1, -2, -3) were activated as well or better by Balb/c and class Ia deficient naïve splenocytes pulsed with uvMoPn as by syngeneic naïve C57BL/6 pulsed with uvMoPN, consistent with not being conventionally-restricted by MHC class Ia molecules.

Whether the CD8 T cell clones were MHC class Ia restricted was tested by comparing activation of mock-pulsed and UV-inactivated *C. muridarum*-pulsed irradiated naïve splenocytes from C57BL/6 (wild type H-2$^b$) and K$^b$D$^b$ dual knockout mice (H-2$^b$; no MHC class Ia molecules) (FIG. 2). K$^b$D$^b$ knockout splenocytes lacking MHC class Ia molecules were as competent as wild type splenocytes for activating three of the CD8 T cell clones, 8sAg1, 8sAg2, 8sAg3; while 8uvmo-2 and 8uvmo-3 were not significantly activated by antigen-pulsed naïve splenocytes. The majority of CD8 T cell clones (3 of 5) were not restricted by MHC class Ia.

Example 6. The CD8 Clones have Varying Abilities to Terminate *Chlamydia* Replication in Epithelial Cells

Figure 4:
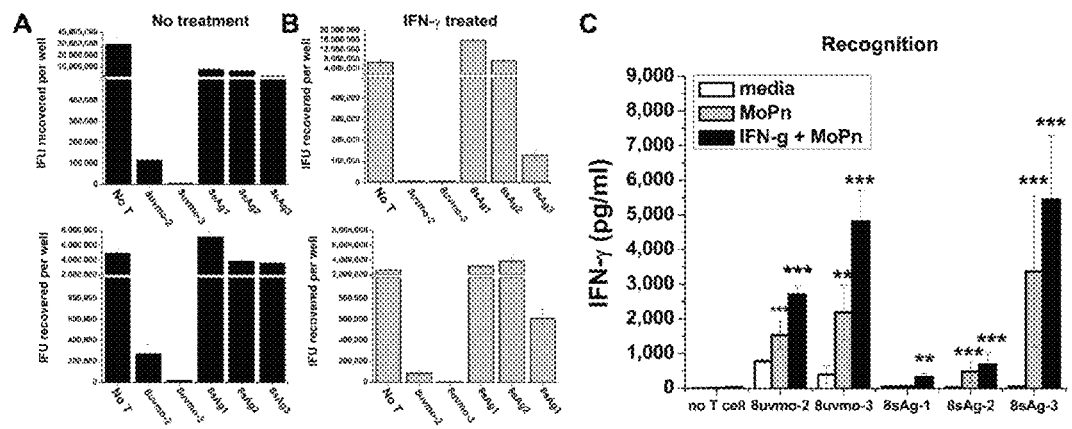
FIG. 4 shows CD8 T cell clones ability to terminate *C. muridarum* replication in upper reproductive tract epithelial cells. C57epi.1 cells, untreated (subpart A) or pretreated with 10 ng IFN-γ (10 ng/ml for 10 h) (subpart B), were infected with 3 IFU *C. muridarum* per cell. 4 h later the inocula were removed, monolayers washed; then T cells were added. Wells were harvested 32 h post-infection and recovered IFU quantified on McCoy monolayers. Top panels of (subpart A) and (subpart B)=experiment #1; bottom panels of (subpart A) and (subpart B)=experiment #2. For IFU values below 100,000, actual recovered IFU are shown immediately above the data bars. Subpart C) Supernatants in experiments #1 and #2 (shown in subparts A and B of FIG. 4) were collected immediately prior to harvesting monolayers; IFN-γ levels were determined by ELISA. Aggregate data from experiments #1 and #2. *=p value <0.05; =p value <0.005; *=p value <0.0005. Conclusion: All CD8 T cell clones recognized infected epithelial cells, with variable ability to terminate *Chlamydia* replication.

*Chlamydia*-specific CD4 T cell clones have varying abilities to terminate *Chlamydia* replication in epithelial cells. The ability of the CD8 T cell clones to terminate *Chlamydia* replication was tested in epithelial cells. C57epi.1 cells, untreated or pretreated with IFN-γ, were infected with *C. muridarum* at 3 IFU per cell. Four hours later the inocula were removed, monolayers washed, and T cell clones added to each well at an effector to target ratio of ~0.75:1. Wells were harvested at 32 h post infection and recovered IFU quantified on McCoy monolayers (FIG. 4, subparts a & b). 8uvmo-2 and 8uvmo-3 were potent terminators of *C. muridarum* replication, with or without IFN-γ pretreatment of the epithelial monolayer. 8sAg1, 8sAg2, and 8sAg3 were entirely unable to control replication, and IFN-γ pretreatment improved the efficiency of only 8sAg3, and it only modestly. Relative ability to terminate *C. muridarum* replication did not correlate cleanly with IFN-γ produced during interaction with infected epithelial cells (FIG. 4, subpart c).

Example 7. The CD8 Clones have Multifunctional Cytokine Profiles Including Production of IL-13 by Two Clones The cytokine profiles of the CD8 T cell clones were investigated using wells coated with anti-CD3 antibody. 24 h supernatants were collected and analyzed for levels of IL-2, IL-10, IL-13, IL-17, IFN-γ, and TNFα by ELISA (FIG. 3). All the clones produced significant amounts of IFN-γ and TNFα, with varying amounts of IL-2; three clones produced large amounts of IL-10, and two significant amounts of IL-13; 8uvmo-2 made a trace amount of IL-17. These multifunctional cytokine patterns do not fall neatly into existing paradigms for CD8 T cell cytokine polarization. IL-13 has been shown to be detrimental to clearance of *Chlamydia muridarum* as determined by genome copy number in mouse lungs and genital tract (Asquith et al, 2013, Plos Path 7:e1001339).

Discussion

CD8 T cell subsets have a role in protection and immunopathology during *Chlamydia* genital tract infections. Experiments utilizing adoptive transfer of *Chlamydia*-specific CD8 T cell lines and clones into chronically infected nude mice demonstrated that CD8 T cells are capable of clearing genital tract infections. Subsequent research utilizing knockout mice revealed that MHC class II (class II knockout) was critical while MHC class I (β2 microglobulin knockout) and CD4 (CD4 knockout) were nonessential for clearing the genital tract. A follow up study using CD4 and CD8 depletions prior to secondary infectious challenge in B cell deficient mice supported the importance of CD4 T cells and identified a role for B cells in clearing *C. muridarum* from the genital tract, without demonstrating a protective effect of *Chlamydia*-specific CD8 T cells that were presumably generated during the primary infection. Those studies did not exclude the possibility that development of protective CD8 T cell immunity is dependent on both CD4 T cells (MHC class II knockout mice) and antibody (T cell depletions in B cell deficient mice). An important technical hurdle for derivation of CD8 T cell clones in this study was a requirement for immune splenocyte presentation of *Chlamydia* antigens; the two CD8 clones that efficiently terminated *C. muridarum* replication in epithelial cells recognized immune splenocytes but not naïve splenocytes pulsed with *C. muridarum*.

Without wishing to be bound by theory, the mechanism underlying the immune splenocytes requirement likely involves one of two known antigen presentation mechanisms. The first is an antigen concentrating mechanism wherein specific antibody efficiently binds and delivers soluble antigen to the pH-dependent endosome/lysosome exogenous pathway for MHC class II presentation. B cells specific for the hapten 2,4,6-trinitrophenyl (TNP) can activate an MHC class II-restricted T cell hybridoma with 1000-fold less TNP-haptenated cognate antigen than naïve B cells. Similarly, IgG specific for tetanous toxoid (TT) improved the efficiency of monocyte-derived dendritic cell activation of TT-specific human CD4 T cell clones by 100-fold. The second mechanism involves delivery of exogenous antigen into an otherwise inaccessible MHC class I presentation pathway. Murine dendritic cells could not cross present physiological concentrations of soluble antigen to an MHC class I-restricted T cell hybridoma, but could cross present IgG-complexed antigen via Fc receptors to the same hybridoma; demonstrating a role for IgG and Fc receptors in directing soluble antigen into an otherwise inaccessible MHC class I presentation pathway. Fc receptors and *Chlamydia* specific antibodies have been shown to play a role in *Chlamydia* pathogenesis. *Chlamydia*-specific antibodies increase the ability of naïve splenocyte APC to activate purified immune T cells to make IFN-γ, and mice deficient in Fc receptors lose their protection from secondary infection. Without wishing to be bound by theory, the defect in secondary immunity may be due to less efficient antigen delivery into the exogenous MHC class II antigen presentation pathway, or loss of an MHC class I cross presentation pathway, or both.

As previously noted, the majority of *Chlamydia*-specific CD8 T cells in this report were not restricted by MHC class Ia molecules. Because 8uvmo-2 and 8uvmo-3 were not activated by naïve splenocytes pulsed with UV-inactivated *C. muridarum*, determination was not made as to their MHC restriction elements. However 8sAg1, 8sAg2, and 8sAg3 were sufficiently activated by antigen-pulsed naïve C57BL/6 and $K^bD^b$ knockout splenocytes to draw the conclusion that they are not restricted by MHC class Ia molecules. This finding in the mouse model is consistent with the finding that the majority of *Chlamydia*-specific CD8 T cell clones isolated from humans with *C. trachomatis* infections were not restricted by HLA class Ia molecules.

*Chlamydia* antigens recognized by CD8 T cells are not fully characterized. Gervassi et al showed that a human class Ia-restricted CD8 clone recognized OmcB, and there is evidence for a human CD8 MOMP epitope. In mice Cap1, CrpA and PmpI were identified as containing CD8 epitopes utilizing mice infected intravenously or intraperitoneally with *C. trachomatis* serovar L2. A subset of murine CD8 T cells specific for *C. pneumonia* recognized formylated bacterial peptides in the context of H2-M3, an MHC class Ib molecule. Interestingly, a proteomic approach toward identifying T cell epitopes identified only a single *C. muridarum* peptide from amino acid permease (TC_0653) associated with MHC class Ia molecules, while multiple peptide epitopes were extracted from MHC class II molecules. There is no information regarding *C. trachomatis* or *C. muridarum* antigens recognized by non-class Ia restricted CD8 T cells in humans or mice.

The CD8 T cell clones in this study had varying abilities to terminate *C. muridarum* replication in epithelial cells. 8uvmo-2 and 8uvmo-3 were as potent as the most potent *Chlamydia*-specific CD4 T cell clones in a previous study, while 8sAg1, 8sAg2, and 8sAg3 were unable or inefficient at terminating replication, even when the epithelial monolayers were pretreated with IFN-γ. The greater efficiency of 8uvmo-2 and 8uvmo-3 did not correlate cleanly with their relative production of IFN-γ. Efficient termination of *Chlamydia* replication by 8uvmo-2 and 8uvmo-3 may relate to a iNOS-dependent mechanism or cytolysis of infected epithelial cells in the non-infectious reticulate body stage of infection/replication (<18 h post infection for *C. muridarum*).

A notable finding in this study was that 2 of the 5 CD8 T cell clones produced significant amounts of IL-13 upon activation, along with IL-2, IFN-γ, IL-10 and TNFα. IL-13 has been shown to be detrimental to *C. muridarum* clearance from lung and genital tract as IL-13 knockout mice clear infections more quickly than wild type mice. IL-10 is similarly detrimental to *C. muridarum* clearance from lung, and is associated with increased residual scarring. CD8 T cells producing IL-10, IL-13 and TNFα are interesting with respect to immunopathology because in addition to a role for IL-10 in scarring, the combination of TNFα and IL-13 has been shown to induce expression of TGFβ1 in some cell types; this cytokine combination is the underlying mechanism for bleomycin-induced pulmonary fibrosis and TNBS-induced colonic fibrosis in mouse models. Clinical investigations have shown that IL-13 expressing CD8 T cells may mediate immunopathology in systemic sclerosis, a rheumatologic disorder that manifests as progressive scarring of skin. *Chlamydia*-specific CD8 T cells, making IL-10, IL-13 and TNFα, may contribute to the CD8-mediated immunopathology observed in experimental murine genital tract infections.

Previous studies in the *C. muridarum* mouse model have shown that CD8 T cells are capable of mediating bacterial clearance from the genital tract; however, on the whole, CD8 T cells play a greater role in immunopathology than in protection. This investigation utilizing *Chlamydia*-specific CD8 T cell clones revealed roles in protection and immunopathology. CD8 T cells that may mediate protection, represented by 8uvmo-2 and 8uvmo-3, terminated *C. muridarum* replication in epithelial cells and had a multifunctional cytokine profile that included IFN-γ and TNFα. CD8 T cells that may contribute to immunopathology, represented by 8sAg1 and 8sAg3, were not restricted by MHC class Ia, were relatively ineffective at terminating *C. muridarum* replication in epithelial cells, and had a cytokine profile including IL-10, TNFα and IL-13. IL-13 production did not cleanly identify poor terminators of *Chlamydia* replication in epithelial cells as IL-$13^{neg}$ 8sAg2 was also ineffective. More importantly, CD8/TNFα-immunopathology has been shown to be a cytokine-mediated event unrelated to bacterial clearance. Because IL-13 and TNFα synergize to induce expression of the scarring-associated cytokine TGFβ in some cell types, IL-13 may play a role in CD8/TNFα-mediated *Chlamydia* immunopathology. A better understanding of CD8 T cells producing IL-13 in the genital tract provides useful insights into *Chlamydia*-associated immunopathology.

Example 8. Human Homolog of Mouse 1810011H11Rik

Patients with systemic sclerosis (scleroderma) were shown to have significant expression of CD8IL-13 biomarker C10orf128, the human homolog of mouse 1810011H11Rik, in their peripheral blood as compared to control patients and patients with acute *Chlamydia* infections (FIG. 9). During acute *Chlamydia* infection CD8IL-13 T cells are localized to the site of infection (i.e., not present in peripheral blood). However, scleroderma is a chronic disseminated inflammatory process; in this setting, there is an expansion of relevant T cell subsets in peripheral blood.

Accordingly, C10orf128 positive CD8 T cells were sorted from human blood using a rabbit anti-C10orf128 anti-serum pursuant to the methodologies described herein. 59,000 viable C10orf128 positive CD8 cells were obtained in about 90 minutes. Unactivated, circulating T cells have low mRNA levels, requiring roughly 150,000 cells (longer sort) to obtain sufficient RNA for microarray analysis. However, 50,000 cells are sufficient to perform RNA isolation and gene expression microarray analysis when the T cells are activated overnight with phorbol 12-myristate 13-acetate+A23187 (ionophore). In a healthy control, C10orf128 positive CD8 T cells are about 0.2% to about 0.4% of the circulating CD8 T cell pool (FIG. 10; see gate P6). Notably, and as extrapolated from the data shown in FIG. 9, the scleroderma patients had C10orf128 mRNA levels as high or higher in their circulating CD8 T cell pool than the healthy controls, likely reducing the total number of CD8 T cells necessary in scleroderma patients to sort sufficient C10orf128 positive CD8 T cells for comparison with C10orf128 negative T cells in gene expression microarray analyses. At the time of filing, there existed no other way to isolate or purify these T cells.

The rabbit antisera used to effectively sort C10orf128 positive CD8 T cells from human blood was made against a peptide having an amino acid sequence comprising QVLATGKTPGAEIDFKY (SEQ. ID NO. 1), or a functional equivalent, variant or fragment thereof. Sequence ID No. 1 is the human homolog of the mouse CD8IL-13 cell surface biomarker 1810011H11Rik predicted extracellular domain. Accordingly, the C10orf128 antibody of the antisera is related to a cell surfaced domain peptide for biomarker C10orf128 and, thus, is capable of recognizing SEQ. ID No. 1, or a functional equivalent, variant or fragment thereof.

Resulting antiserum may be cross absorbed against a scrambled peptide to improve specificity. Among other things, this C10orf128-specific antisera allows for the development of novel diagnostics and interventions for scleroderma and *Chlamydia* infections. For example, purified C10orf128 positive and negative CD8 T cells from scleroderma patients can now be subjected to gene expression microarray analysis to identify unique targets for scleroderma-specific diagnostics and possible targets for therapeutic interventions.

Referring back to SEQ. ID NO. 1, additionally or alternatively, a cysteine may be added to SEQ. ID No. 1 to couple SEQ. ID No. 1 to a keyhole limpet hemocyanin (KHL) (e.g., CQVLATGKTPGAEIDFKY). It will be appreciated that alternative coupling strategies could also be employed (including, but not limited to, C-terminal coupling) such that the peptide can be covalently attached to a carrier protein and used for immunization purposes.

C10orf128 and/or the rabbit antisera described herein may be used to identify a subset of CD8 T cells that make IL-13 upon activation or to purify from peripheral blood a subset of CD8 T cells that make IL-13 upon activation.

It will be recognized by one of skill in the art that homologs of the biomarkers described herein may be similarly used to identify and/or purify a subset of CD8 T cells that make IL-13 upon activation (e.g., mouse 1810011H11Rik and its human analog C10orf128). For example, in at least one exemplary application, one of skill in the art could use the methodologies and techniques described herein to purify CD8 T cells from SSc patients or other human subjects, activate such cells (using one or more of the methodologies described herein including, but not limited to, immobilized anti-CD3, PMA/ionophores), and sort the cells based on the human homologs of the mouse "activated" CD8IL-13 cell surface biomarkers Tm4sf19 or 1830127L07Rik.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the present disclosure was illustrated using specific examples, theoretical arguments, accounts and illustrations, these illustrations and the accompanying discussion should by no means be interpreted as limiting the technology.

The invention claimed is:

1. A method of isolating a subset of CD8 T cells that produce interleukin-13 upon activation, the method comprising the steps of:

obtaining a sample of lymphocytes from a mammal;

activating the sample of lymphocytes with immune-irradiated splenocytes to obtain a polyclonal T cell clone population, wherein the immune-irradiated splenocytes present an antigen recognized by the sample of lymphocytes;

expanding the polyclonal T cell clone population;

selectively depleting the CD4 T cell clones present in the polyclonal T cell clone population to isolate an activated CD8 T cell clone population;

measuring gene expression in the activated CD8 T cell clone population;

determining if any of the activated CD8 T cell clone population expresses an elevated level of a biomarker as compared to a healthy control, the biomarker selected from a group consisting of: 1810011H11Rik and C10orf128; and isolating a subset of CD8 T cell clones that express the elevated level of the biomarker from the activated CD8 T cell population;

wherein the elevated level of the biomarker is indicative of interleukin-13 production by the subset of CD8 T cells.

2. The method of claim 1, wherein:

the biomarker comprises C10orf128;

the mammal comprises a human; and the steps of determining if any of the activated CD8 T cell clone population expresses an elevated level of the biomarker and isolating a subset of CD8 T cell clones that express the elevated level of the biomarker from the activated CD8 T cell clone population further comprise:

using an anti-C10orf128 antiserum to identify the subset of CD8 T cell clones that express the elevated level of C10orf128;

wherein the anti-C10orf128 antiserum is made against a peptide having an amino acid sequence comprising SEQ ID NO: 1, or a functional equivalent, variant, or fragment thereof, attached to a carrier protein.

3. The method of claim 2, wherein the carrier protein attached to the peptide comprises a keyhole limpet hemocyanin.

4. The method of claim 1, wherein the antigen comprises a UV-inactivated *Chlamydia muridarum* or elementary body-depleted soluble *Chlamydia muridarum* antigen preparation.

5. The method of claim 1, wherein the step of determining if any of the activated CD8 T cell clone population expresses an elevated level of the biomarker as compared to a healthy control is applicable to the diagnosis of one or more disease states.

6. The method of claim 5, wherein at least one of the disease states comprises scarring associated with a *Chlamydia* infection or systemic sclerosis.

* * * * *

SEQUENCE LISTING

```
<160> NUMBER OF SEQ ID NOS: 1

<210> SEQ ID NO 1
<211> LENGTH: 17
<212> TYPE: PRT
<213> ORGANISM: Artificial Sequence
<220> FEATURE:
<223> OTHER INFORMATION: Predicted human CD8IL-13-specific peptide
      capable of binding the cell surface domain of human CD8IL-13
      biomarker C10orf128

<400> SEQUENCE: 1

Gln Val Leu Ala Thr Gly Lys Thr Pro Gly Ala Glu Ile Asp Phe Lys
1               5                   10                  15

Tyr
```